(12) United States Patent
Lee et al.

(10) Patent No.: US 10,197,218 B2
(45) Date of Patent: Feb. 5, 2019

(54) MEDICAL APPARATUS, AND DISPLAY SUPPORTING STRUCTURE AND ARM STRUCTURE USED IN THE SAME

(71) Applicant: SAMSUNG ELECTRONICS CO., LTD., Suwon-si, Gyeonggi-do (KR)

(72) Inventors: Jae-won Lee, Seoul (KR); Jea-eun Shin, Seoul (KR); Sok-jae Shin, Yongin-si (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 0 days.

(21) Appl. No.: 15/808,332

(22) Filed: Nov. 9, 2017

(65) Prior Publication Data

US 2018/0135797 A1  May 17, 2018

(30) Foreign Application Priority Data

Nov. 17, 2016 (KR) .................. 10-2016-0153316

(51) Int. Cl.
*F16M 13/00* (2006.01)
*F16M 13/02* (2006.01)
(Continued)

(52) U.S. Cl.
CPC .......... *F16M 13/02* (2013.01); *A61B 5/7445* (2013.01); *A61B 6/462* (2013.01); *A61B 8/462* (2013.01);
(Continued)

(58) Field of Classification Search
CPC ........ F16M 13/02; F16M 11/10; F16M 11/38; F16M 11/04; F16M 2200/041;
(Continued)

(56) References Cited

U.S. PATENT DOCUMENTS

| 4,682,749 A | 7/1987 | Stater |
| 5,213,293 A * | 5/1993 | Muentener ............. F16M 11/10 |
| | | 248/123.11 |

(Continued)

FOREIGN PATENT DOCUMENTS

| JP | 2005-526567 | 9/2005 |
| JP | 2008-126015 | 6/2008 |

(Continued)

OTHER PUBLICATIONS

Extended European Search Report dated Apr. 24, 2018 issued in European Patent Application No. 17199644.0.

(Continued)

*Primary Examiner* — Anita M King
(74) *Attorney, Agent, or Firm* — McDermott Will & Emery LLP (57) ABSTRACT

A medical apparatus includes an elastic compensation member providing a first link that is rotatable with respect to a first rotational axis so that a display apparatus is movable, with a torque in an opposite direction to a torque acting due to a load of the display apparatus in order to compensate for the torque acting due to the load of the display apparatus, in order to minimize a length variation of the elastic compensation member despite movement of the display apparatus, a first end portion of the elastic compensation member is not fixed to the first link but is supported by an additional rotatable supporting portion so that the first end portion of the elastic compensation member is movable relative the first link while the display apparatus is being moved.

20 Claims, 10 Drawing Sheets

(51) Int. Cl.
  *A61B 5/00* (2006.01)
  *A61B 6/00* (2006.01)
  *A61B 8/00* (2006.01)
  *F16M 11/10* (2006.01)
  *F16M 11/38* (2006.01)
  *F16M 11/04* (2006.01)

(52) U.S. Cl.
  CPC ............. *F16M 11/10* (2013.01); *F16M 11/38* (2013.01); *F16F 2230/0011* (2013.01); *F16M 11/04* (2013.01); *F16M 2200/041* (2013.01); *F16M 2200/063* (2013.01)

(58) Field of Classification Search
  CPC ............ F16M 2200/063; A61B 5/7445; A61B 6/462; A61B 8/462; F16F 2230/0011
  See application file for complete search history.

(56) References Cited

U.S. PATENT DOCUMENTS

| | | | | |
|---|---|---|---|---|
| 5,288,043 | A * | 2/1994 | Tigliev | A61B 90/25 248/123.11 |
| 6,543,914 | B2 * | 4/2003 | Sander | F16M 11/08 362/401 |
| 6,663,569 | B1 | 12/2003 | Wilkins et al. | |
| 7,562,851 | B2 * | 7/2009 | Hein | F16M 11/2014 248/276.1 |
| 8,348,845 | B2 | 1/2013 | Ninomiya et al. | |
| 8,870,141 | B2 * | 10/2014 | Abri | F16M 11/14 248/281.11 |
| 9,314,306 | B2 * | 4/2016 | Yu | A61B 6/12 |
| 9,657,889 | B1 | 5/2017 | Chumakov | |
| 2003/0086240 | A1 | 5/2003 | Jobs et al. | |
| 2012/0138754 | A1 | 6/2012 | Lim | |
| 2012/0223199 | A1 * | 9/2012 | Abri | F16M 11/14 248/280.11 |
| 2015/0231018 | A1 | 8/2015 | Shim et al. | |

FOREIGN PATENT DOCUMENTS

| | | |
|---|---|---|
| KR | 10-2007-0097737 | 10/2007 |
| KR | 10-1656614 | 9/2016 |
| WO | 2011/154703 A2 | 12/2011 |
| WO | 2011/155934 A1 | 12/2011 |

OTHER PUBLICATIONS

Notice of Allowance dated Jan. 24, 2018, in corresponding Korean Patent Application No. 10-2016-0153316.

* cited by examiner

MEDICAL APPARATUS, AND DISPLAY SUPPORTING STRUCTURE AND ARM STRUCTURE USED IN THE SAME

CROSS-REFERENCE TO RELATED APPLICATION

This application claims the benefit of Korean Patent Application No. 10-2016-0153316, filed on Nov. 17, 2016, in the Korean Intellectual Property Office, the disclosure of which is incorporated herein in its entirety by reference.

BACKGROUND

1. Field

The present disclosure relates to a medical apparatus, and a display supporting structure and arm structure used in the medical apparatus.

2. Description of the Related Art

A medical apparatus such as an ultrasound diagnosis apparatus may include a medical image acquiring unit transmitting an ultrasound to an object and receiving another ultrasound reflected from the object and a display apparatus displaying an image generated using the medical image acquiring unit.

The medical apparatus may further include an arm structure that movably supports the display apparatus so that a user can easily view the display apparatus. The arm structure is rotatable with respect to a predetermined rotational axis, thereby enabling the display apparatus to be moved up and down.

In order to facilitate manipulation of the display apparatus when moving it, the arm structure may further include an elastic compensation member providing a torque acting in an opposite direction to a torque applied to a rotational axis due to the load of the display apparatus.

However, while moving the display apparatus, the torque provided by the elastic compensation member may be changed, and accordingly, compensation deviation between the torque acting due to the load of the display apparatus and the torque acting due to the elastic compensation member is increased.

SUMMARY

Provided are a medical apparatus having a structure for minimizing compensation deviation between a torque provided by an elastic compensation member and a torque acting due to the load of a display apparatus, and a display supporting structure, and an arm structure.

Additional aspects will be set forth in part in the description which follows and, in part, will be apparent from the description, or may be learned by practice of the presented embodiments.

According to an aspect of an embodiment, a medical apparatus includes a medical image acquiring unit, a display apparatus displaying information obtained from the medical image acquiring unit, and an arm structure movably supporting the display apparatus, wherein the arm structure includes a base part, a movement frame where a load of the display apparatus to be applied to the movement frame, a first link to connect the movement frame and the base part, the first link being rotatably connected with respect to a first rotational axis to the base part so that the movement frame is movable relative to the base part, and a first torque acts on the first rotational axis due to the load being applied to the movement frame, an elastic compensation member elastically deformable and having a first end portion connected to the base part, the elastic compensation member providing the first rotational axis with a second torque acting in an opposite direction to the first torque in order to compensate for the first torque; a compensation member supporting portion having a first end portion that is rotatably connected to a second rotational axis of the movement frame and a second end portion that is movable relative to the first link and supports a second end portion of the elastic compensation member which is not fixed to the first link, and a distance variation guide configured to vary a distance between the second end portion of the elastic compensation member and the first link in a direction perpendicular to a length direction of the first link, wherein while the movement frame is being moved, the first link is rotated with respect to the first rotational axis, and the compensation member supporting portion rotates with respect to the second rotational axis, and the second end portion of the elastic compensation member is moved with respect to the first link in the length direction of the first link and in the direction perpendicular to the length direction of the first link.

A first connection point to which the base part and the first link are connected and a second connection point to which the base part and the elastic compensation member are connected may be spaced apart from each other.

A third connection point to which the first link and the movement frame are connected and a fourth connection point to which the compensation member supporting portion and the movement frame may be connected are spaced apart from each other.

While the first link is being rotated with respect to the first rotational axis, a distance between the first connection point and the second end portion of the elastic compensation member in the length direction of the first link and a distance between the first connection point and the second end portion of the elastic compensation member in the direction perpendicular to the length direction of the first link may vary.

The distance variation guide may be in the first link and has an inclined surface having a height varying in the direction perpendicular to the length direction of the first link along the length direction of the first link, wherein the compensation member supporting portion further includes a circular roller at the second end portion of compensation member supporting portion, wherein the roller of the compensation member supporting portion moves along the inclined surface.

The inclined surface may be on an inner portion of the first link and have a height that varies from a virtual line connecting the first connection point and the third connection point in the direction perpendicular to the length direction of the first link.

A height of the inclined surface may vary linearly or non-linearly in the direction perpendicular to the length direction of the first link.

The distance variation guide may further include a cam that is at the second end portion of the compensation member supporting portion and is rotatable along the first link.

The medical apparatus may further include a second link that is parallel to the first link and has a first end portion connected to the base part and a second end portion connected to the movement frame.

A distance between a fifth connection point to which the second link and the movement frame are connected and the third connection point may be identical to a distance between a sixth connection point to which the second link and the base part are connected and the first connection point.

Two end portions of the first link and the second link may be pivotable relative to the base part and the movement frame, wherein while the first link is being rotated with respect to the first rotational axis, a screen direction of the display apparatus is maintained uniform.

According to an aspect of another embodiment, a display supporting structure includes a display apparatus and an arm structure movably supporting the display apparatus, wherein the arm structure includes a base part, a movement frame where a load of the display apparatus to be applied to the movement frame, a first link to connect the movement frame and the base part, the first link being rotatably connected with respect to a first rotational axis of the base part so that the movement frame is movable relative to the base part and a first torque acts on the first rotational axis due to the load being applied to the movement frame, an elastic compensation member elastically deformable and having a first end portion connected to the base part, the elastic compensation member providing the first rotational axis with a second torque acting in an opposite direction to the first torque in order to compensate for the first torque, a compensation member supporting portion having a first end portion that is rotatably connected to a second rotational axis of the movement frame and a second end portion that is movable with respect to the first link and supports a second end portion of the elastic compensation member which is not fixed to the first link, and a distance variation guide configured to vary a distance between the second end portion of the elastic compensation member and the first link in a direction perpendicular to a length direction of the first link, wherein while the movement frame is being moved, the first link is rotated with respect to the first rotational axis, and the compensation member supporting portion rotates with respect to the second rotational axis, and the second end portion of the elastic compensation member is moved with respect to the first link in the length direction of the first link and in the direction perpendicular to the length direction of the first link.

A first connection point to which the base part and the first link are connected and a fourth connection point to which the base part and the compensation member supporting portion are connected may be spaced apart from each other.

While the first link is being rotated with respect to the first rotational axis, a distance between the first connection point and the second end portion of the elastic compensation member in the length direction of the first link and a distance between the first connection point and the second end portion of the elastic compensation member in the direction perpendicular to the length direction of the first link may vary.

The distance variation guide may be in the first link and have an inclined surface having a height varying in the direction perpendicular to the length direction of the first link along the length direction of the first link, wherein the compensation member supporting portion further includes a circular roller at the second end portion of the compensation member supporting portion, wherein the roller of the compensation member supporting portion moves along the inclined surface.

The distance variation guide may further include a cam that is at the second end portion of the compensation member supporting portion and is rotatable along the first link.

The display supporting structure may further include a second link that is parallel to the first link and has a first end portion connected to the base part and a second end portion connected to the movement frame, wherein a third connection point to which the first link and the movement frame are connected and a fourth connection point to which the compensation member supporting portion and the movement frame are connected are spaced apart from each other.

A distance between a fifth connection point to which the second link and the movement frame are connected and the third connection point may be identical to a distance between a sixth connection point to which the second link and the base part are connected and the first connection point.

Two end portions of each of the first link and the second link may be pivotable relative to the base part and the movement frame, wherein while the first link is being rotated with respect to the first rotational axis, a screen direction of the display apparatus is maintained uniform.

According to an aspect of another embodiment, an arm structure includes a base part, a movement frame where a predetermined load to be applied to the movement frame, a first link to connect the movement frame and the base part, the first link being rotatably connected with respect to a first rotational axis of the base part so that the movement frame is movable relative to the base part, and a first torque acts on the first rotational axis due to the load being applied to the movement frame, an elastic compensation member elastically deformable and having a first end portion connected to the base part, the elastic compensation member providing the first rotational axis with a second torque acting in an opposite direction to the first torque in order to compensate for the first torque, a compensation member supporting portion having a first end portion that is rotatably connected to a second rotational axis of the movement frame and a second end portion that is movable with respect to the first link and supports a second end portion of the elastic compensation member, which is not fixed to the first link and a distance variation guide configured to vary a distance between the second end portion of the elastic compensation member and the first link in a direction perpendicular to a length direction of the first link, wherein while the movement frame is being moved, the first link is rotated with respect to the first rotational axis, and the compensation member supporting portion rotates with respect to the second rotational axis, and the second end portion of the elastic compensation member is moved with respect to the first link in the length direction of the first link and in the direction perpendicular to the length direction of the first link.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. Expressions such as "at least one of," when preceding a list of elements, modify the entire list of elements and do not modify the individual elements of the list.

The present disclosure will now be described more fully for clarity of the scope of the present disclosure and such that one of ordinary skill in the art may easily work the present disclosure. This present disclosure may, however, be embodied in many different forms.

Throughout the specification, wherein like reference numerals denote like elements. Not every element of embodiments are described in the present application, and general knowledge in the field to which the present disclosure pertains or repeated description between embodiments will be omitted. In addition, terms such as " . . . part", " . . . portion" may be implemented as software or hardware, and according to embodiments, a plurality of "parts" or "portions" may be implemented as a single unit or element, and a single "part" or "portion" may include a plurality of elements. Hereinafter, the functional principle of the present disclosure and embodiments thereof will be described with reference to the attached drawings.

In the present specification, an image may include medical images captured using a medical imaging apparatus such as a magnetic resonance imaging (MRI) apparatus, a computed tomography (CT) apparatus, a ultrasound imaging apparatus or an X-ray imaging apparatus.

In the present specification, an "object" refers to an object of photography and may be a human, an animal, or a part of a human or animal. For example, the object may include a part of body (e.g., an organ) or a phantom.

Hereinafter, example embodiments will be described in detail.

Figure 1:
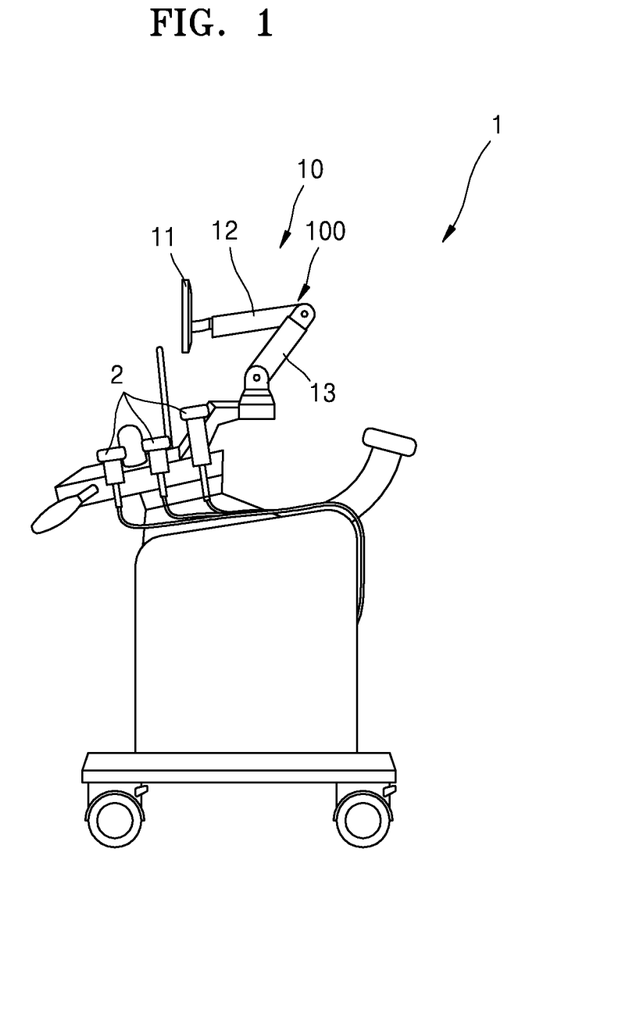
FIG. 1 is a side view of a medical apparatus according to an example embodiment.
Figure 2A:
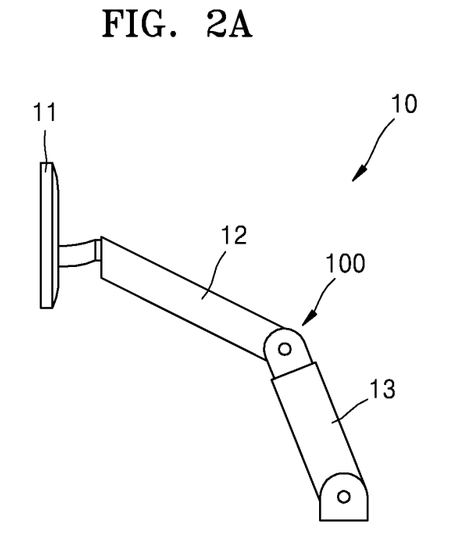
FIGS. 2A and 2B are views for explaining location movement of a display apparatus in the medical apparatus of FIG. 1.
Figure 2B:
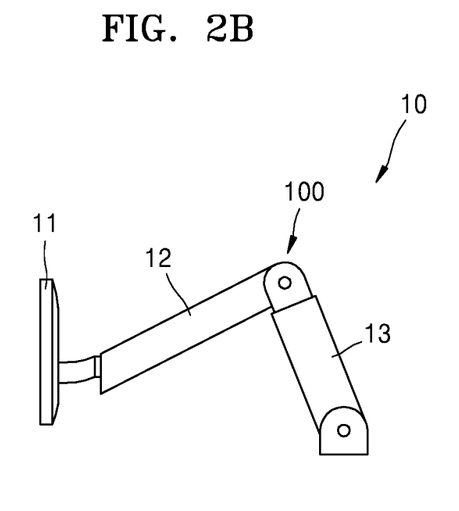

FIG. 1 is a side view of a medical apparatus 1 according to an example embodiment. FIGS. 2A and 2B are views for explaining location movement of a display apparatus 11 in the medical apparatus 1 of FIG. 1.

Referring to FIG. 1, the medical apparatus 1 according to the example embodiment may include a medical image acquiring unit 2 and a display supporting structure 10. The display supporting structure 10 includes a display apparatus 11 and an arm structure 100.

The medical image acquiring unit 2 irradiates an object and may receive radiation that has passed through an object or reflected by an object. The radiation may be an ultrasound, but is not limited thereto, and may also be another type of radiation for diagnosis, for example, an X-ray.

The display apparatus 11 displays information obtained using the medical image acquiring unit 2. The display apparatus 11 may display a radiation image such as an ultrasound image. However, the radiation image is not limited thereto, and may also be an image for diagnosis of an object, for example, an X-ray image. A weight of the display apparatus 11 may be about 2 kg to about 10 kg.

The arm structure 100 movably supports the display apparatus 11. For example, the arm structure 100 supports the display apparatus 11 such that the display apparatus 11 is movable in a vertical direction up and down as illustrated in FIGS. 2A and 2B.

The arm structure 100 may be a foldable structure. For example, the arm structure 100 includes a first arm 12 supporting the display apparatus 11 and a second arm 13 that pivotably supports the first arm 12.

The display apparatus 11 may be mounted at an end portion of the first arm 12. Diagnosis information about an object may be displayed by using the display apparatus 11. The second arm 13 may be pivotable relative to a main body of the medical apparatus 1.

The arm structure 100 may have a structure in which the first arm 12 and the second arm 13 are unfolded to be away from each other as illustrated in FIG. 2A or the first arm 12 and the second arm 13 approach each other as illustrated in FIG. 2B.

When a manipulation force by a user acts on the display apparatus 11, the display apparatus 11 may be moved via the arm structure 100. The display apparatus 11 may be moved not only up and down but also back and forth.

Figure 3A:
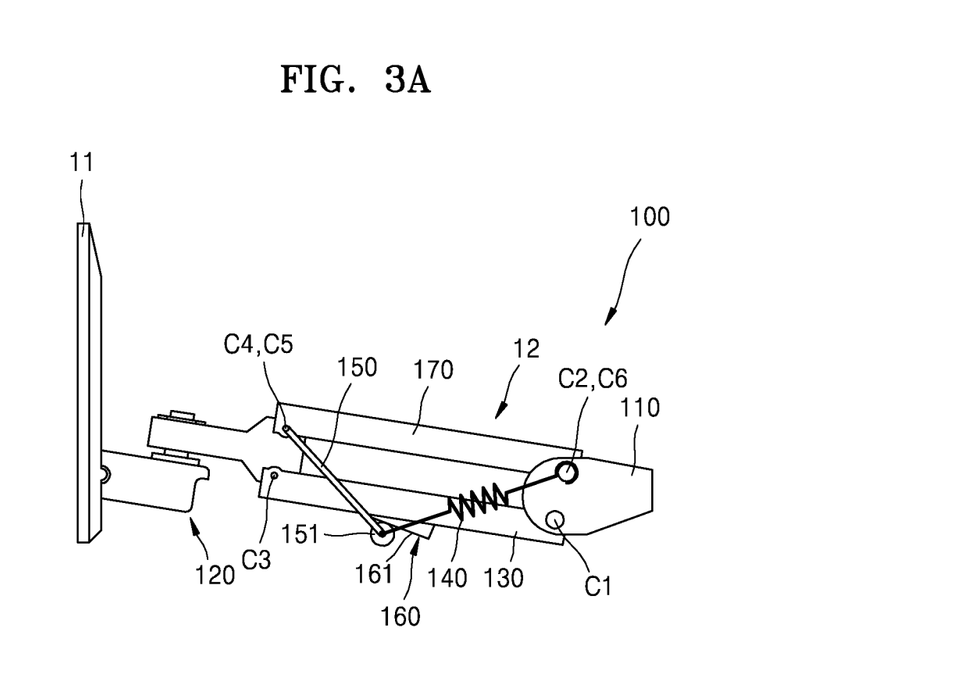
FIG. 3A is a view focusing on a first arm that movably supports a display apparatus in an arm structure disclosed in FIG. 1.
Figure 3B:
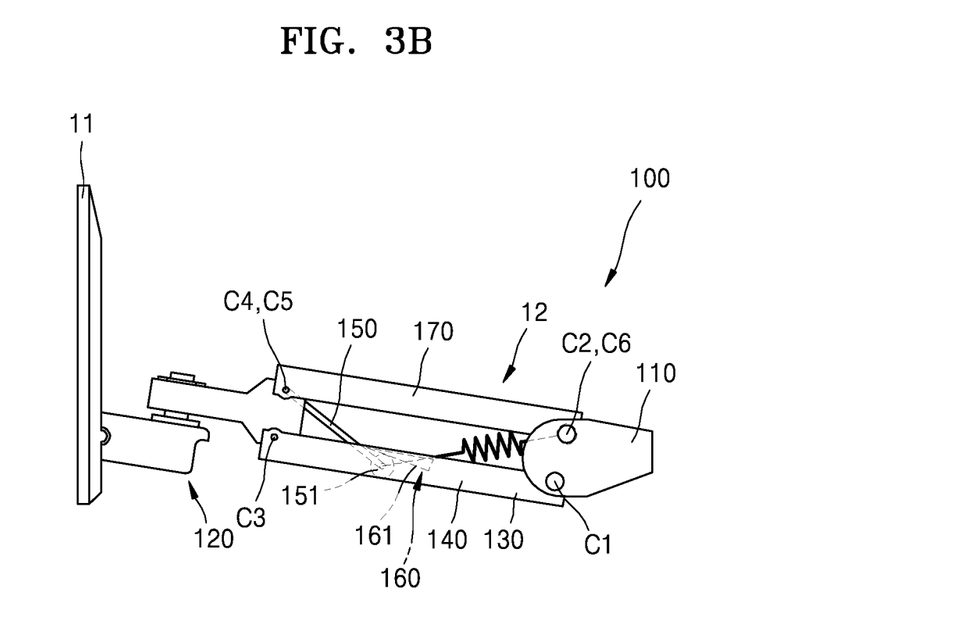
FIG. 3B illustrates a modified example of the arm structure of FIG. 3A.
Figure 4:
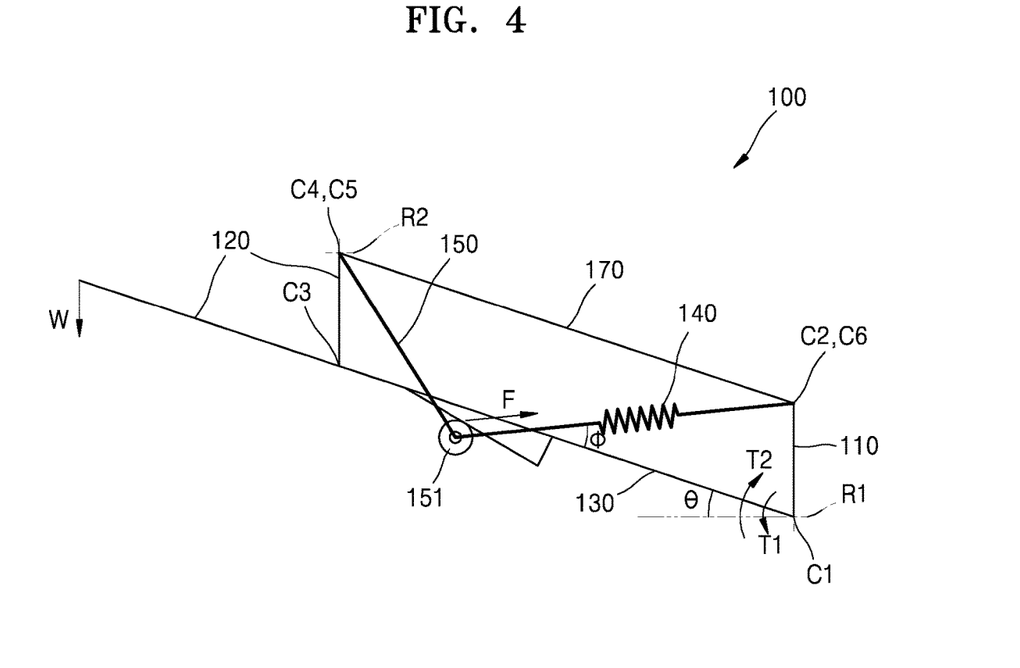
FIG. 4 is a conceptual diagram of the arm structure of FIG. 3A.

FIG. 3A is a view focusing on the first arm 12 that movably supports the display apparatus 11 in the medical apparatus 1 disclosed in FIG. 1. FIG. 3B illustrates a modified example of the arm structure 100 of FIG. 3A. FIG. 4 is a conceptual diagram of the arm structure 100 of FIG. 3A. In FIGS. 3A and 3B, for convenience of description, the arm structure 100 from which a cover thereof is removed is illustrated.

Referring to FIGS. 3A and 4, the first arm 12 is rotatably supported with respect to a base part 110 of the second arm 13. The arm structure 100 according to the embodiment includes the base part 110, a movement frame 120, a first link 130, and an elastic compensation member 140.

The display apparatus 11 is mounted at an end portion of the movement frame 120, and a load of the display apparatus 11 acts on the end portion of the movement frame 120. The movement frame 120 is movable relative to the base part 110.

The first link 130 is disposed between the movement frame 120 and the base part 110, and connects the movement frame 120 and the base part 110 to each other. The first link 130 is rotatably connected to the base part 110 with respect to a first rotational axis R1 such that the movement frame 120 is movable relative to the base part 110.

A first end portion of the first link 130 is connected to the base part 110, and a second end portion of the first link 130 is connected to the movement frame 120. As the second end portion of the first link 130 is connected to the movement frame 120, due to a load of the display apparatus 11 acting on the movement frame 120, a first torque T1 is applied to the first rotational axis R1.

The elastic compensation member 140 is elastically deformable, and provides a second torque T2 acting in an opposite direction to the first torque T1 to the first rotational axis R1 so as to compensate for the first torque T1. A first end portion of the elastic compensation member 140 is connected to the base part 110, and provides a predetermined elastic force to the first link 130 via a second end portion of the elastic compensation member 140. A first connection point C1 to which the base part 110 and the first link 130 are connected and a second connection point C2 to which the base part 110 and the elastic compensation member 140 are connected are spaced apart from each other.

Through the second torque T2 provided by the elastic compensation member 140, the first torque T1 acting on the first rotational axis R1 may be offset, thereby enabling a user to move the display apparatus 11 with a relatively small force.

A modulus of elasticity of the elastic compensation member 140 may be selected by considering the first torque T1. The modulus of elasticity may be a spring constant if the elastic compensation member 140 is a spring. For example, when an angle (θ) of the first link 130 in a horizontal direction with respect to the first rotational axis R1 is a predetermined angle, for example, 0 degree (°), a modulus of elasticity of the elastic compensation member 140 may be selected by considering the first torque T1 acting on the first rotational axis R1.

In a case where the angle (θ) of the first link 130 is fixed to 0 degree, the first torque T1 is set by a weight W of the display apparatus 11 and a distance between the first rotational axis R1 and a point to which the weight W of the display apparatus 11 is applied.

The second torque T2 provided by the elastic compensation member 140 to the first rotational axis R1 may be determined by an elastic force F of the elastic compensation member 140, an angle (φ) between the elastic compensation member 140 and the first link 130, and a distance between the first rotational axis R1 and a point to which the elastic force F of the elastic compensation member 140 is applied. The elastic force F of the elastic compensation member 140 is determined by a modulus of elasticity of the elastic compensation member 140 and a length variation of the elastic compensation member 140.

A modulus of elasticity of the elastic compensation member 140 may be designed such that the second torque T2 offsets the first torque T1.

While moving the display apparatus 11, the movement frame 120 supporting the display apparatus 11 is moved, and the first link 130 movably supporting the movement frame 120 is rotated with respect to the first rotational axis R1. In a case where an end portion of the elastic compensation member 140 is fixed to the first link 130, while the first link 130 is rotated, a length of the elastic compensation member 140 providing a predetermined elastic force F to the first link 130 is varied.

Due to the variation in the length of the elastic compensation member 140, the elastic force F of the elastic compensation member 140 may be varied. A variation in the elastic force F of the elastic compensation member 140 may be varied according to a modulus of elasticity of the elastic compensation member 140. In other words, even if a length variation of the elastic compensation member 140 is uniform, the higher a modulus of an elasticity of the elastic compensation member 140, the greater is a variation in the elastic force F.

The elastic compensation member 140 may be a member used inside the arm structure 100 that movably supports the display apparatus 11 in the medical apparatus 1. As the arm structure 100 has a relatively narrow internal space, an allowable length variation of the elastic compensation member 140 may be small. On the other hand, an elastic force F required to compensate for a predetermined load of the display apparatus 11 may be large. In order to fulfill these two requirements, the elastic compensation member 140 may have a high modulus of elasticity. For example, a modulus of elasticity of the elastic compensation member 140 may be about three to four times a modulus of elasticity of an elastic compensation member that is generally used to mount the arm structure 100. For example, a modulus of elasticity of the elastic compensation member 140 actually needed for mounting may be 0.5 kgf/mm or greater. However, a modulus of the elastic compensation member 140 may be 5 kgf/mm or less.

As such, if a modulus of elasticity of the elastic compensation member 140 high, despite a small length variation of the elastic compensation member 140, a variation in an elastic force of the elastic compensation member 140 may be large. According to the variation in the elastic force of the elastic compensation member 140, a variation in the second torque T2 provided by the elastic compensation member 140 to the first rotational axis R1 may be increased.

By considering this, in the arm structure 100 of the embodiment, in order to reduce a variation in the second torque T2 generated during rotation of the first link 130, a structure that allows to reduce a variation in a length of the elastic compensation member 140 during rotation of the first link 130 is provided. To this end, for example, a compensation member supporting portion 150 that supports the second end portion of the elastic compensation member 140 such that the second end portion of the elastic compensation member 140 is not fixed to the first link 130 but is movable is further included.

A first end portion of the compensation member supporting portion 150 is rotatably connected with respect to the second rotational axis R2 of the movement frame 120. A third connection point C3 to which the first link 130 and the movement frame 120 are connected and a fourth connection point C4 to which a supporting portion of the elastic compensation member 140 and the movement frame 120 are connected may be spaced apart from each other.

A second end portion of the compensation member supporting portion 150 is movable relative to the first link 130, and supports the second end portion of the elastic compensation member 140. The second end portion of the elastic compensation member 140 is not fixed to the first link 130 but is supported by the second end portion of the compensation member supporting portion 150.

While a location of the movement frame 120 is moved, the compensation member supporting portion 150 is rotated with respect to the second rotational axis R2, and the second end portion of the elastic compensation member 140 that is supported by the second end portion of the compensation member supporting portion 150 may be moved relative to the first link 130. As a location of the second end portion of the elastic compensation member 140 is moved, a distance between the second end portion of the elastic compensation member 140 and the first rotational axis R1 in a length direction of the first link 130 may be varied.

Figure 5:
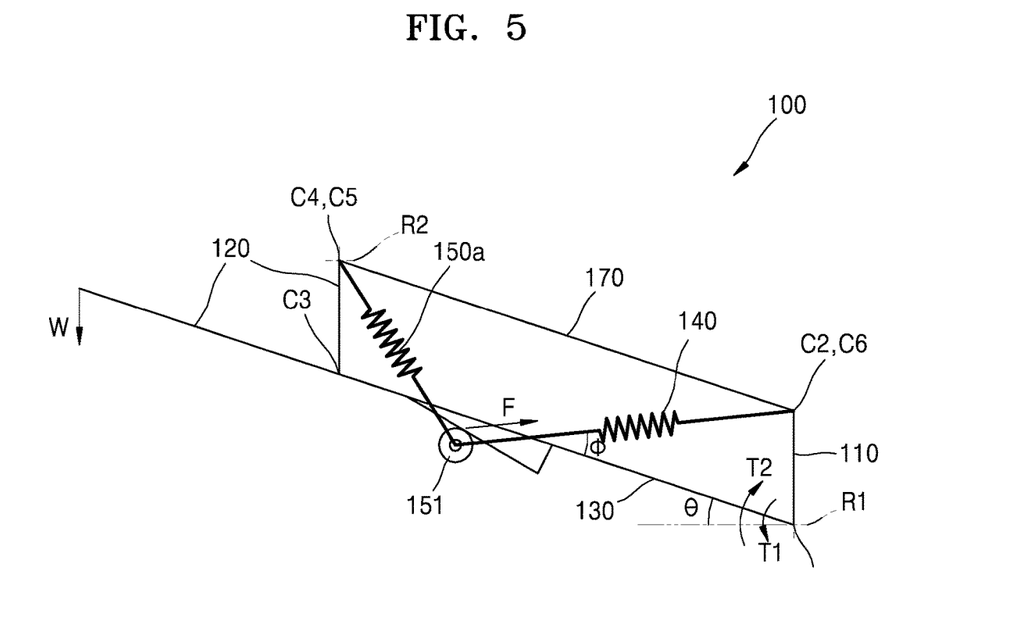
FIG. 5 is a conceptual diagram of an arm structure according to another example embodiment.

The compensation member supporting portion 150 may be in a link form having a uniform length. However, the compensation member supporting portion 150 is not limited thereto, and may have a variously modified shape as long as the first end portion of the compensation member supporting portion 150 is rotatable with respect to the second rotational axis R2 and the second end portion thereof is movable and supports the second end portion of the elastic compensation member 140. For example, as illustrated in FIG. 5, a compensation member supporting portion 150a may be an elastic member formed to be elastically deformable.

Figure 6:
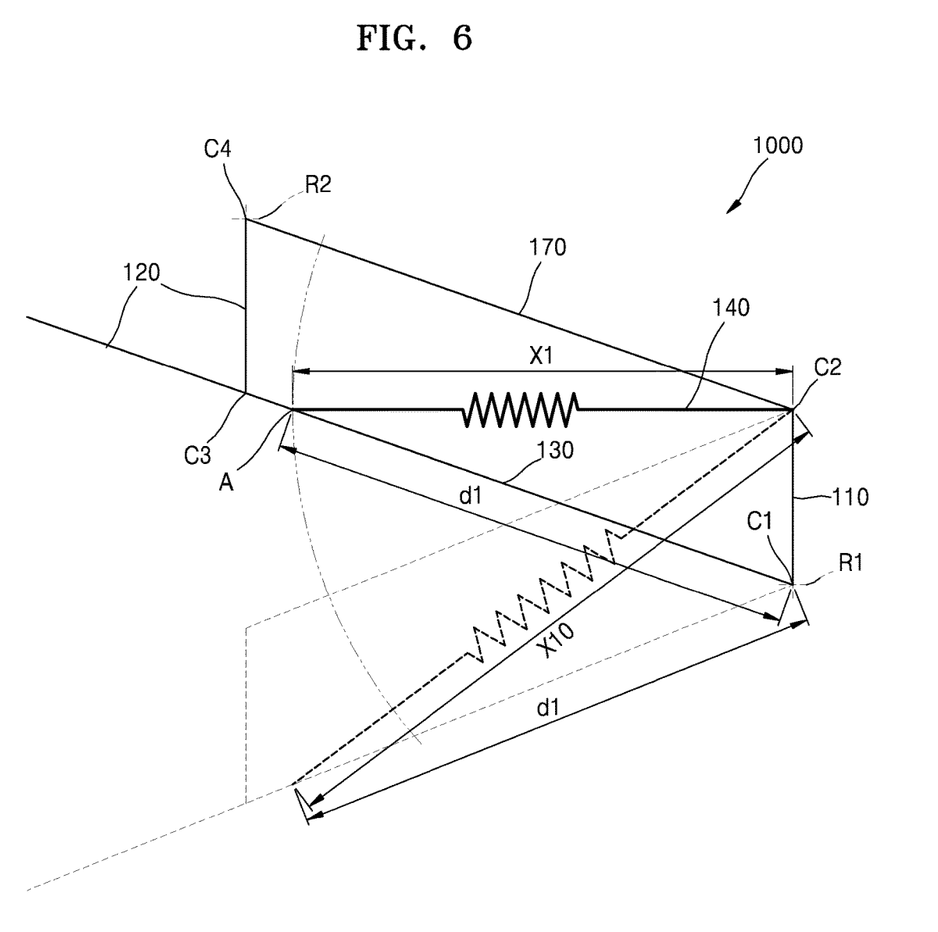
FIG. 6 is a conceptual diagram of an operation of an arm structure in which a second end portion of an elastic compensation member is fixed to a first link, according to a comparative example.
Figure 7:
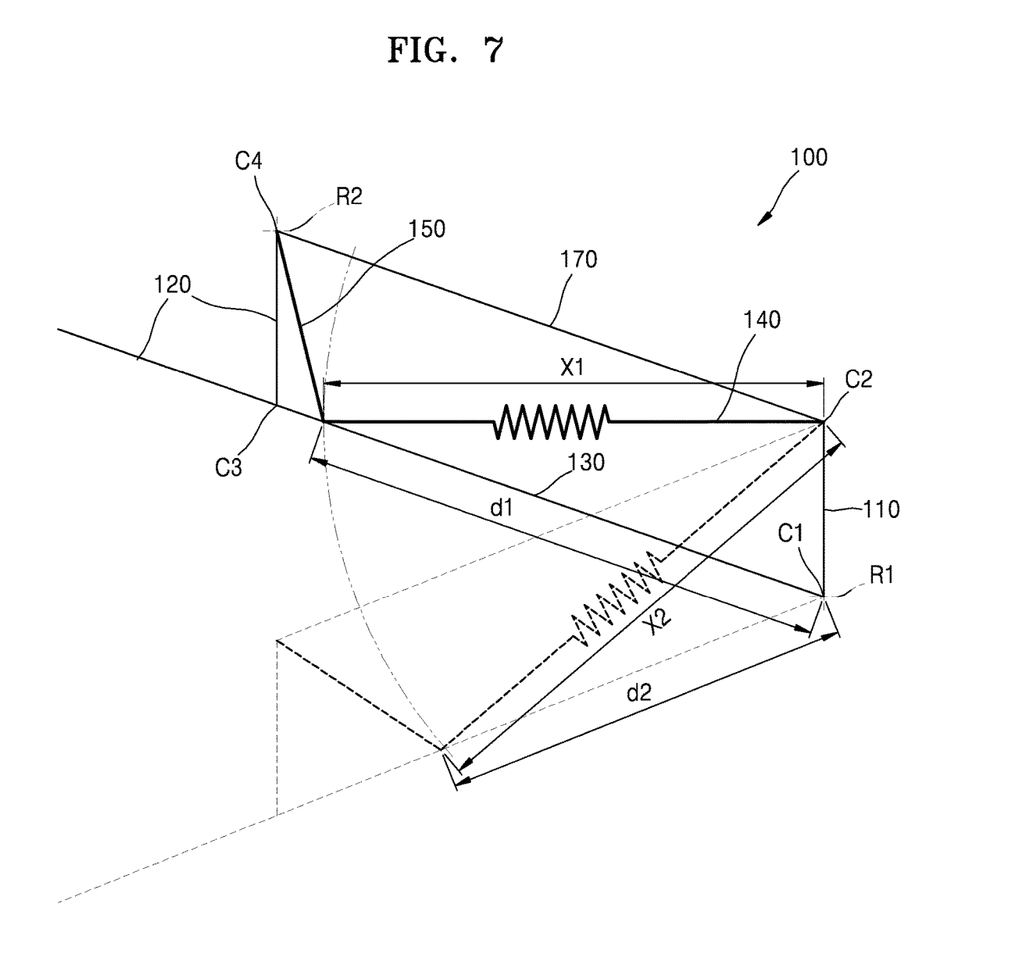
FIG. 7 is a conceptual diagram of an operation of an arm structure in which a second end portion of an elastic compensation member is movable, according to an example embodiment.

FIG. 6 is a conceptual diagram of an operation of an arm structure 1000 according to a comparative example, in which a second end portion of an elastic compensation member 140 is fixed to a first link 130. FIG. 7 is a conceptual diagram of an operation of the arm structure 100 according to the example embodiment, in which a second end portion of the elastic compensation member 140 is movable.

Referring to FIG. 6, in the arm structure 1000 according to the comparative example, a first end portion of the elastic compensation member 140 is connected to the second connection point C2, and the second end portion of the elastic compensation member 140 is fixed to a fixing point A of the first link 130. As the second end portion of the elastic compensation member 140 is connected to the fixing point A of the first link 130, if the first link 130 is rotated with respect to the first rotational axis R1, the second end portion of the elastic compensation member 140 also rotates when the fixing point A of the first link 130 is rotated. Accordingly, a length X1 of the elastic compensation member 140 is changed to a length X10. A distance d1 between the second end portion of the elastic compensation member 140 and the first rotational axis R1 in a length direction of the first link 130 is constant.

Referring to FIG. 7, in the arm structure 100 according to the example embodiment, the first end portion of the elastic compensation member 140 is connected to the second connection point C2, and the second end portion of the elastic compensation member 140 is not fixed to the first link 130 but is movable. According to the example embodiment, as the second end portion of the elastic compensation member 140 is not fixed to the first link 130, even when the first link 130 is rotated, the length X10 of the elastic compensation member 140 (see FIG. 6) is changed to a length X2 which is shorter than the length X10. Here, the distance d1 between the second end portion of the elastic compensation member 140 and the first rotational axis R1 in the length direction of the first link 130 may be changed to a distance d2.

As described above, according to the arm structure 100 according to the example embodiment, as the second end portion of the elastic compensation member 140 is movable relative to the first link 130 in the length direction of the first link 130, despite rotation of the first link 130, a length variation of the elastic compensation member 140 may be reduced. For example, a length variation of the elastic compensation member 140 having the second end portion that is movable relative to the first link 130 in the present embodiment is reduced compared to a length variation of the elastic compensation member 140 having the second end portion that is fixed with respect to the first link 130. For example, a length variation of the elastic compensation member 140 according to the present embodiment may be reduced by about 30% compared to a length variation of an elastic compensation member having a second end portion that is fixed. In addition, for example, a length variation of the elastic compensation member 140 may be 10% or less of a length of the elastic compensation member 140 when an angle of the first link 130 with respect to a horizontal direction is 0 degree. As described above, by reducing a length variation of the elastic compensation member 140, a variation in the second torque T2 provided by the elastic compensation member 140 may be reduced.

Figure 8:
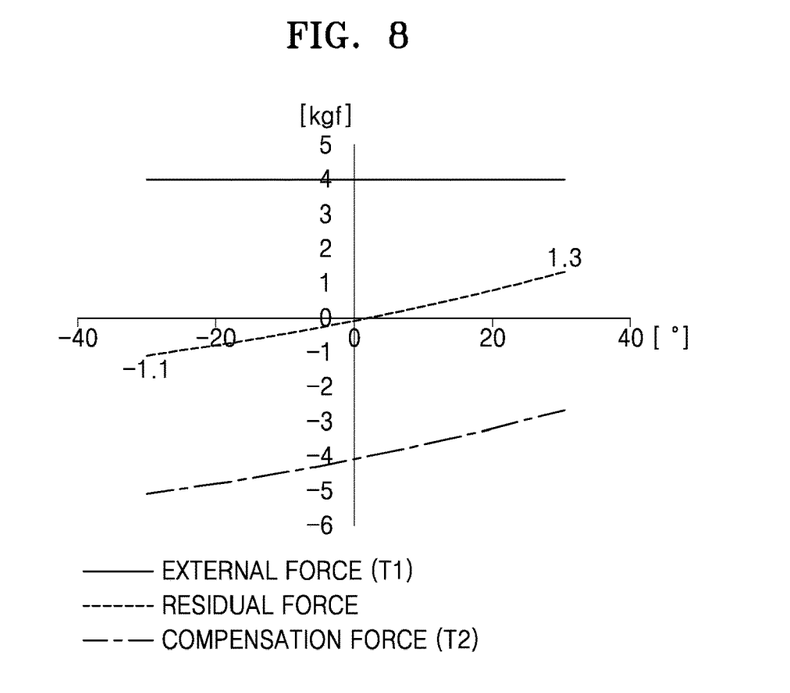
FIG. 8 is a view for describing a deviation in a compensation force due to the elastic compensation member in an arm structure according to the comparative example of FIG. 6.
Figure 9:
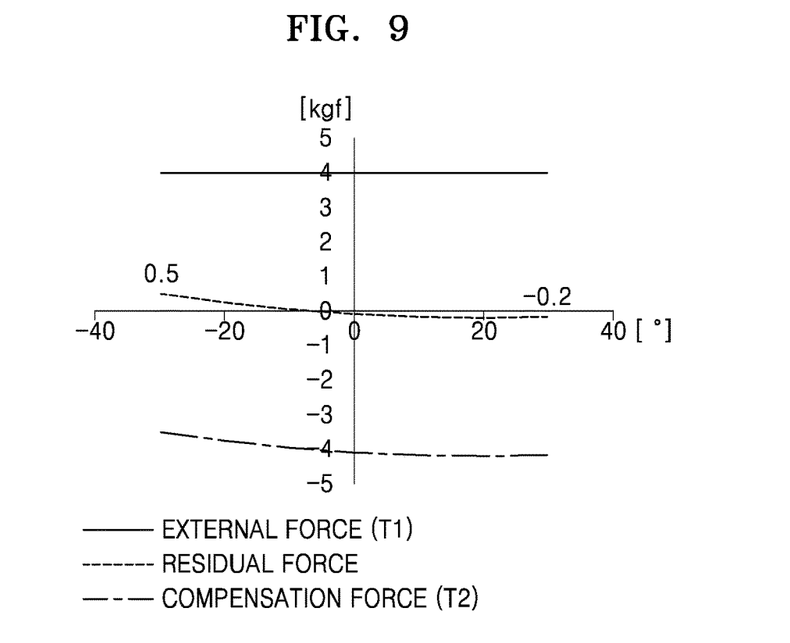
FIG. 9 is a view for describing a deviation in a compensation force due to the elastic compensation member in an arm structure according to the example embodiment of FIG. 7.

FIG. 8 is a view for describing a deviation in a compensation force due to the elastic compensation member 140 in the arm structure 1000 according to the comparative example of FIG. 6. FIG. 9 is a view for describing a deviation in a compensation force due to the elastic compensation member 140 in the arm structure 100 according to the example embodiment of FIG. 7. For reference, in FIGS. 8 and 9, to describe a difference between the comparative example and the example embodiment, for convenience, values of the first torque T1 and the second torque T2, in which an influence of an angle of the first link 130 is not reflected, are shown.

Referring to FIG. 8, in the arm structure 1000 according to the comparative example, the second torque T2 provided by the elastic compensation member 140 during rotation of the first link 130 is about 2.7 kgf to about 5.1 kgf in an opposite direction to the first torque T1. Accordingly, when an angle of the first link 130 is +30 degrees, the second torque T2 is smaller than the first torque T1 by 1.3 kgf, whereas if an angle of the first link 130 is −30 degrees, the second torque T2 is greater than the first torque T1 by 1.1 kgf.

On the other hand, referring to FIG. 9, in the arm structure 100 of the embodiment, the second torque T2 provided by the elastic compensation member 140 during rotation of the first link 130 is about 3.5 kgf to about 4.2 kgf in an opposite direction to the first torque T1. Accordingly, when an angle of the first link 130 is +30 degrees, the second torque T2 is greater than the first torque T1 by 0.2 kgf, whereas if an angle of the first link 130 is −30 degrees, the second torque T2 is greater than the first torque T1 by 0.5 kgf.

In other words, in the arm structure 100 of the example embodiment, by reducing a length variation of the elastic compensation member 140, a deviation between the second torque T2 provided by the elastic compensation member 140 and the first torque T1 may be remarkably reduced. For example, a deviation between the second torque T2 and the first torque T1 may be reduced to 1 kgf or less. For example, a deviation between the second torque T2 and the first torque T1 may be reduced to 0.5 kgf or less.

Referring back to FIGS. 3A and 4, the arm structure 100 according to the example embodiment further includes a distance variation guide 160 configured to vary a distance between the first connection point C1 and the second end portion of the elastic compensation member 140 in a direction perpendicular to the length direction of the first link 130.

As the first link 130 is rotated, an angle between a horizontal direction with respect to the first rotational axis R1 and the first link 130 is varied, and an angle between the elastic compensation member 140 and the first link 130 is varied. Accordingly, each of an amount of the first torque T1 and an amount of the second torque T2 is varied. As described above, in order to make the first torque T1 and the second torque T2, which are variable, correspond to each other, the distance variation guide 160 may be used to vary a distance between the first connection point C1 and the second end portion of the elastic compensation member 140 in a direction perpendicular to the length direction of the first link 130.

For example, the distance variation guide 160 may be disposed in the first link 130, and may have an inclined surface 161 having a height that varies in the direction perpendicular to the length direction of the first link 130, along the length direction of the first link 130.

Figure 10A:
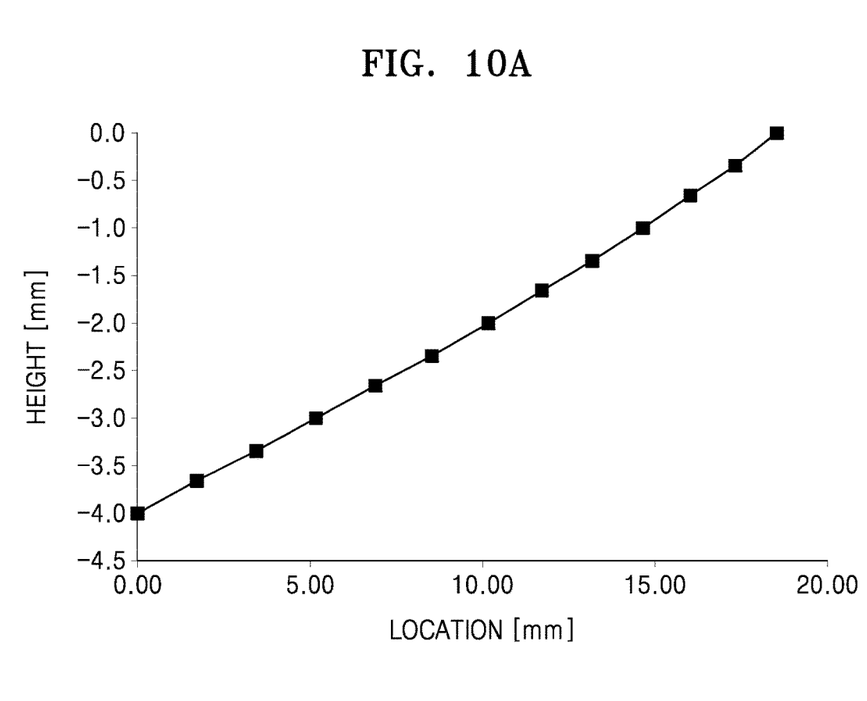
FIG. 10A illustrates a variation in a height of an inclined surface of a first link in a length direction, for explaining example embodiments of an inclined surface of a distance variation guide of FIG. 3A.
Figure 10B:
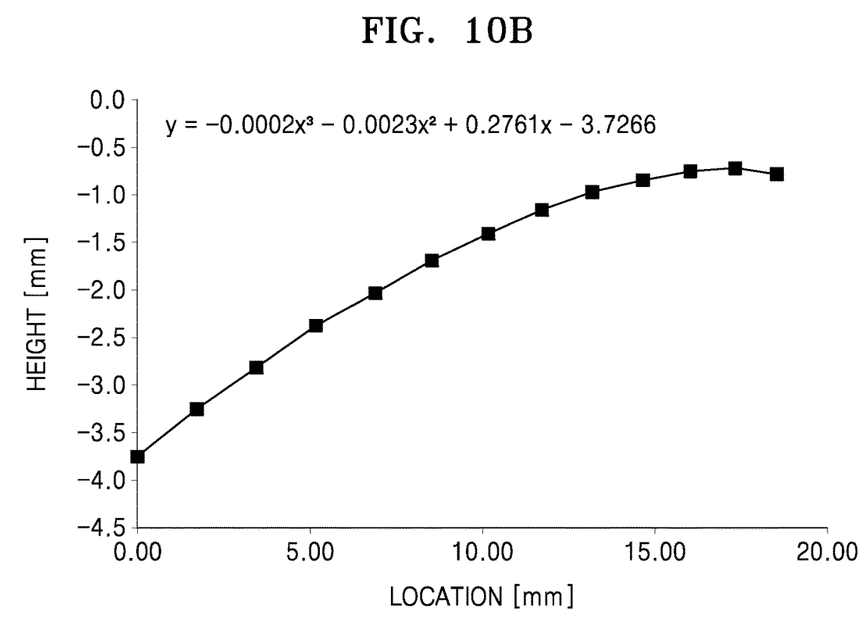
FIG. 10B illustrates a variation in a height of an inclined surface of a first link in a length direction, for explaining a modified example of an inclined surface of a distance variation guide of FIG. 3A.

FIG. 10A illustrates a variation in a height of inclined surfaces 161 and 161a in a length direction of the first link 130 for explaining example embodiments of the inclined surface 161 of FIG. 3A. FIG. 10B illustrates a variation in a height of an inclined surface of a first link in a length direction, for explaining a modified example of an inclined surface of a distance variation guide of FIG. 3A. Here, x denotes a location of the inclined surface 161 in a length direction of the first link 130, and y denotes a height of the inclined surface 161. For reference, along a y-axis, a negative (−) symbol is used for a height of the inclined surface 161 below a height of the first connection point C1 and the third connection point C3 of the first link 130.

Referring to FIG. 10A, the inclined surface 161 may be formed to have a linearly varying height in a direction perpendicular to the length direction of the first link 130 along the length direction of the first link 130. For example, a height variation of the inclined surface 161 may be linear.

However, design of the inclined surface 161 is not limited thereto, and by considering required compensation force, the inclined surface 161 may be designed in various manners. For example, referring to FIG. 10B, the inclined surface 161 may have a height that varies non-linearly in a direction perpendicular to the length direction of the first link 130 along the length direction of the first link 130. For example, a height variation of the inclined surface 161 may be in a curved form. As described above, by designing a curved height variation of the inclined surface 161, a deviation in a compensation force may be set to 20 gf or less.

For example, a height of the inclined surface 161 of FIG. 10B may be determined by a functional formula (1) as below:

$$y = -0.0002x^3 - 0.0023x^2 + 0.2761x - 3.7266 \quad (1)$$

Referring to FIG. 3A again, the inclined surface 161 of the distance variation guide 160 may be disposed to protrude outwardly from the first link 130. However, arrangement of the distance variation guide 160 is not limited thereto, and the distance variation guide 160 may also be disposed inside the first link 130. For example, referring to FIG. 3B, the inclined surface 161 of the distance variation guide 160 may be disposed in the first link 130. In this case, the inclined surface 161 may have a height that varies from a virtual line connecting the first connection point C1 and the third connection point C3 in a direction perpendicular to the length direction of the first link 130.

A roller 151 rotating to move along the inclined surface 161 may be mounted at an end portion of the compensation member supporting portion 150. The roller 151 may have a circular cross-sectional shape.

Figure 11:
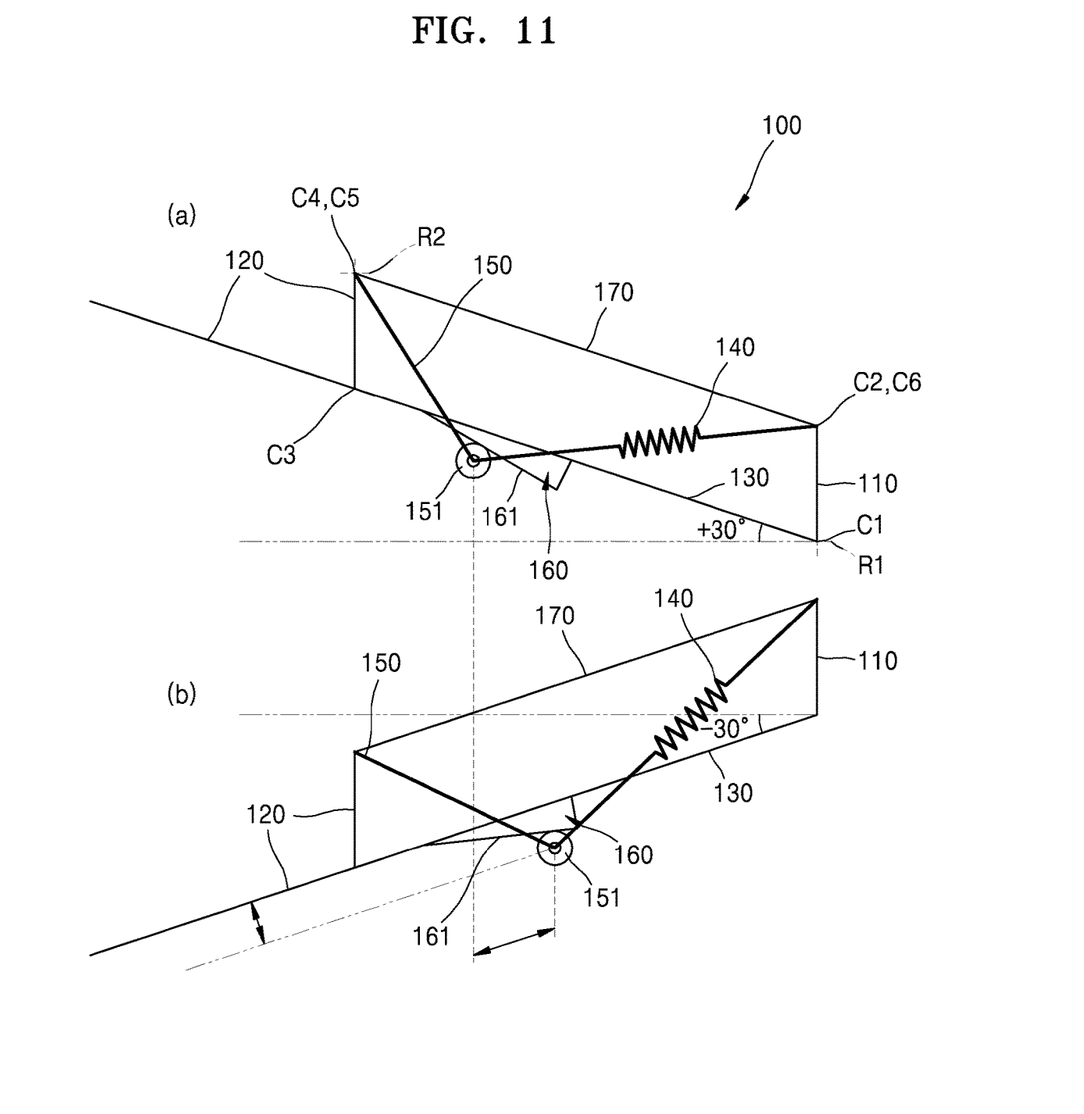
FIG. 11 is a view for describing an operation of a distance variation guide when the first link of FIG. 4 is rotated.

FIG. 11 is a view for describing an operation of the distance variation guide 160 when the first link 130 of FIG. 4 is rotated. Referring to FIG. 11, when the first link 130 is rotated with respect to the first rotational axis R1 by +30 degrees or −30 degrees, the compensation member supporting portion 150 is rotated in a counter-clockwise direction with respect to the second rotational axis R2, and the second end portion of the elastic compensation member 140 supported by the second end portion of the compensation member supporting portion 150 is moved relative to the first link 130. The second end portion of the elastic compensation member 140 is moved from a virtual line connecting the first connection point C1 and the third connection point C3 in a length direction of the first link 130 and in a direction perpendicular to the length direction of the first link 30.

As described above, by movably adjusting the second end portion of the elastic compensation member 140 with respect to multiple directions, a variation of the second torque T2 due to the elastic compensation member 140 occurring during location movement of the movement frame 120 may be designed to correspond to a variation of the first torque T1.

Figure 12:
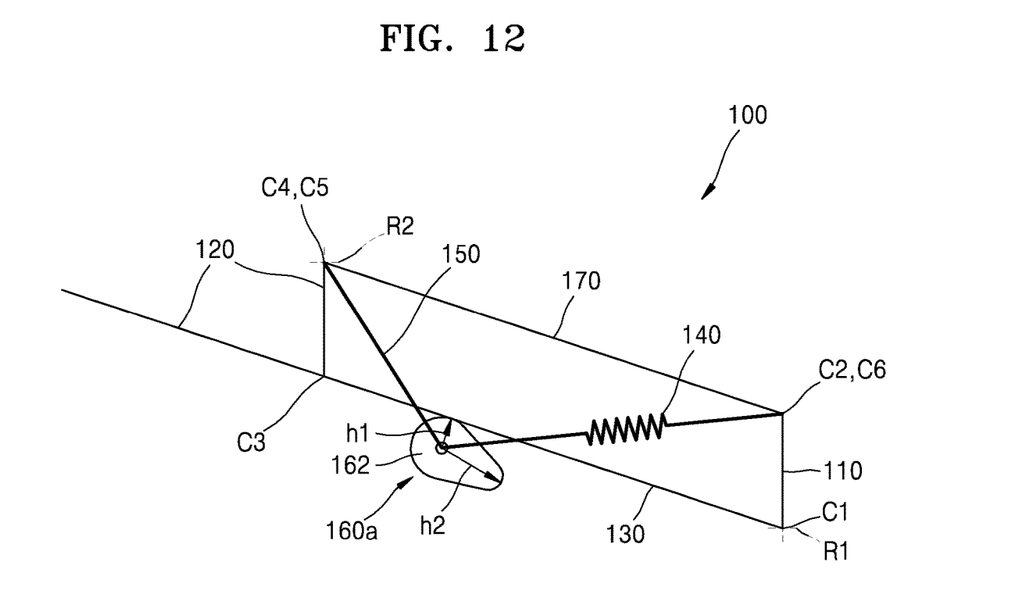
FIG. 12 is a conceptual diagram of an arm structure according to another example embodiment.

However, a structure and arrangement of the distance variation guide 160 is not limited thereto, but may be modified in various manners. For example, as illustrated in FIG. 12, a guide variation guide 160a may be a cam 162 that is rotatable and mounted at the second end portion of the compensation member supporting portion 150. A distance h1 and a distance h2 from a rotational axis of the cam 162 to an external surface thereof vary, and the cam 162 may be rotatable along a surface of the first link 130. The second end portion of the elastic compensation member 140 may be connected to the rotational axis of the cam 162.

As the distances h1 and h2 from the rotational axis of the cam 162 to the surface thereof are varied, during rotation of the cam 162 along the first link 130, a distance between the rotational axis of the cam 162 and the first link 130 may be varied. Accordingly, a distance between the second end portion of the elastic compensation member 140 and the first link 130 in the direction perpendicular to the length direction of the first link 130 may be varied.

Referring back to FIGS. 3A, 4, and 7, the arm structure 100 may further include a second link 170 that is parallel to the first link 130 and has a first end portion connected to the base part 110 and a second end portion connected to the movement frame 120.

A distance between a fifth connection point C5 to which the second link 170 and the movement frame 120 are connected and the third connection point C3 may be identical to a distance between a sixth connection point C6 to which the second link 170 and the base part 110 are connected and the first connection point C1. The fifth connection point C5 may be identical to the fourth connection point C4, and the sixth connection point C6 may be identical to the second connection point C2. However, the fifth and sixth connection points C5 and C6 may not necessarily be identical to the fourth connection point C4 and the second connection point C2, respectively, and may be different points according to necessity.

Two end portions of the first link 130 may be pivotable relative to the base part 110 and the movement frame 120, and two end portions of the second link 170 may be pivotable relative to the base part 110 and the movement frame 120.

Accordingly, while the first link 130 and the second link 170 rotate with respect to the base part 110 so that the movement frame 120 is moved, a screen direction of the display apparatus 11 mounted on the movement frame 120 may be maintained uniform.

Figure 13:
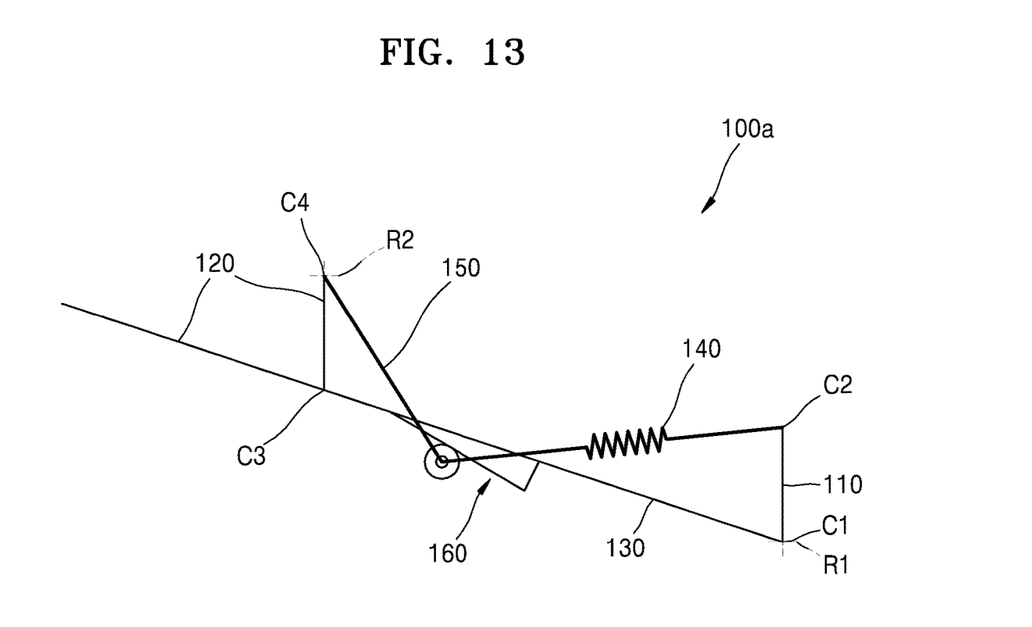
FIG. 13 is a conceptual diagram of an arm structure according to another example embodiment.

However, the arm structure 100 of the example embodiment does not necessarily have to include the second link 170, and the second link 170 may be omitted according to necessity. For example, if a screen direction of the display apparatus 11 does not have to be maintained uniform by using a link structure, an arm structure 100a may not include the second link 170 as illustrated in FIG. 13.

According to the medical apparatus, and the display supporting structure and the arm structure of the example embodiments, by minimizing a length variation of the elastic compensation member according to location movement of the display apparatus, compensation deviation between a torque provided by the elastic compensation member and a torque acting due to a load of the display apparatus may be reduced.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A medical apparatus comprising a medical image acquiring unit, a display apparatus displaying information obtained from the medical image acquiring unit, and an arm structure movably supporting the display apparatus,
   wherein the arm structure comprises:
   a base part;
   a movement frame where a load of the display apparatus to be applied thereto;
   a first link to connect the movement frame and the base part, the first link being rotatably connected with respect to a first rotational axis of the base part so that the movement frame is movable relative to the base part, and a first torque acts on the first rotational axis due to the load being applied to the movement frame;
   an elastic compensation member elastically deformable and having a first end portion connected to the base part, the elastic compensation member providing the first rotational axis with a second torque acting in an opposite direction to the first torque in order to compensate for the first torque;
   a compensation member supporting portion having a first end portion that is rotatably connected to a second rotational axis of the movement frame and a second end portion that is movable relative to the first link and supports a second end portion of the elastic compensation member which is not fixed to the first link; and
   a distance variation guide configured to vary a distance between the second end portion of the elastic compensation member and the first link in a direction perpendicular to a length direction of the first link,
   wherein while the movement frame is being moved, the first link is rotated with respect to the first rotational axis, and the compensation member supporting portion rotates with respect to the second rotational axis, and the second end portion of the elastic compensation member is moved with respect to the first link in the length direction of the first link and in the direction perpendicular to the length direction of the first link.

2. The medical apparatus of claim 1, wherein a first connection point to which the base part and the first link are connected and a second connection point to which the base part and the elastic compensation member are connected are spaced apart from each other.

3. The medical apparatus of claim 2, wherein a third connection point to which the first link and the movement frame are connected and a fourth connection point to which the compensation member supporting portion and the movement frame are connected are spaced apart from each other.

4. The medical apparatus of claim 2, wherein while the first link is being rotated with respect to the first rotational axis, a distance between the first connection point and the second end portion of the elastic compensation member in the length direction of the first link and a distance between the first connection point and the second end portion of the elastic compensation member in the direction perpendicular to the length direction of the first link vary.

5. The medical apparatus of claim 3, wherein the distance variation guide is in the first link and has an inclined surface having a height varying in the direction perpendicular to the length direction of the first link along the length direction of the first link, and
   wherein the compensation member supporting portion further comprises a circular roller at the second end portion of compensation member supporting portion,
   wherein the roller of the compensation member supporting portion moves along the inclined surface.

6. The medical apparatus of claim 5, wherein the inclined surface is on an inner portion of the first link and has a height that varies from a virtual line connecting the first connection point and the third connection point in the direction perpendicular to the length direction of the first link.

7. The medical apparatus of claim 5, wherein a height of the inclined surface varies linearly or non-linearly in the direction perpendicular to the length direction of the first link.

8. The medical apparatus of claim 3, wherein the distance variation guide further comprises a cam that is at the second end portion of the compensation member supporting portion and is rotatable along the first link.

9. The medical apparatus of claim 3, further comprising a second link that is parallel to the first link and has a first end portion connected to the base part and a second end portion connected to the movement frame.

10. The medical apparatus of claim 9, wherein a distance between a fifth connection point to which the second link and the movement frame are connected and the third connection point is identical to a distance between a sixth connection point to which the second link and the base part are connected and the first connection point.

11. The medical apparatus of claim 10, wherein two end portions of the first link and the second link are pivotable relative to the base part and the movement frame, and
   wherein while the first link is being rotated with respect to the first rotational axis, a screen direction of the display apparatus is maintained uniform.

12. A display supporting structure comprising a display apparatus and an arm structure movably supporting the display apparatus, wherein the arm structure comprises:
a base part;
a movement frame where a load of the display apparatus to be applied to the movement frame;
a first link to connect the movement frame and the base part, the first link being rotatably connected with respect to a first rotational axis of the base part so that the movement frame is movable relative to the base part and a first torque acts on the first rotational axis due to the load being applied to the movement frame;
an elastic compensation member elastically deformable and having a first end portion connected to the base part, wherein the elastic compensation member providing the first rotational axis with a second torque acting in an opposite direction to the first torque in order to compensate for the first torque;
a compensation member supporting portion having a first end portion that is rotatably connected to a second rotational axis of the movement frame and a second end portion that is movable with respect to the first link and supports a second end portion of the elastic compensation member which is not fixed to the first link; and
a distance variation guide configured to vary a distance between the second end portion of the elastic compensation member and the first link in a direction perpendicular to a length direction of the first link,
wherein while the movement frame is being moved, the first link is rotated with respect to the first rotational axis, and the compensation member supporting portion rotates with respect to the second rotational axis, and the second end portion of the elastic compensation member is moved with respect to the first link in the length direction of the first link and in the direction perpendicular to the length direction of the first link.

13. The display supporting structure of claim 12, wherein a first connection point to which the base part and the first link are connected and a fourth connection point to which the base part and the compensation member supporting portion are connected are spaced apart from each other.

14. The medical apparatus of claim 13, wherein while the first link is being rotated with respect to the first rotational axis, a distance between the first connection point and the second end portion of the elastic compensation member in the length direction of the first link and a distance between the first connection point and the second end portion of the elastic compensation member in the direction perpendicular to the length direction of the first link vary.

15. The display supporting structure of claim 14, wherein the distance variation guide is in the first link and has an inclined surface having a height varying in the direction perpendicular to the length direction of the first link along the length direction of the first link, and
wherein the compensation member supporting portion further comprises a circular roller at the second end portion of the compensation member supporting portion,
wherein the roller of the compensation member supporting portion moves along the inclined surface.

16. The display supporting structure of claim 12, wherein the distance variation guide further comprises a cam that is at the second end portion of the compensation member supporting portion and is rotatable along the first link.

17. The display supporting structure of claim 13, further comprising a second link that is parallel to the first link and has a first end portion connected to the base part and a second end portion connected to the movement frame,
wherein a third connection point to which the first link and the movement frame are connected and a fourth connection point to which the compensation member supporting portion and the movement frame are connected are spaced apart from each other.

18. The display supporting structure of claim 17, wherein a distance between a fifth connection point to which the second link and the movement frame are connected and the third connection point is identical to a distance between a sixth connection point to which the second link and the base part are connected and the first connection point.

19. The display supporting structure of claim 18, wherein two end portions of each of the first link and the second link are pivotable relative to the base part and the movement frame, and
wherein while the first link is being rotated with respect to the first rotational axis, a screen direction of the display apparatus is maintained uniform.

20. An arm structure comprising:
a base part;
a movement frame where a predetermined load to be applied thereto;
a first link to connect the movement frame and the base part, the first link being rotatably connected with respect to a first rotational axis of the base part so that the movement frame is movable relative to the base part and a first torque acts on the first rotational axis due to the load being applied to the movement frame;
an elastic compensation member elastically deformable and having a first end portion connected to the base part, the elastic compensation member providing the first rotational axis with a second torque acting in an opposite direction to the first torque in order to compensate for the first torque;
a compensation member supporting portion having a first end portion that is rotatably connected to a second rotational axis of the movement frame and a second end portion that is movable with respect to the first link and supports a second end portion of the elastic compensation member which is not fixed to the first link; and
a distance variation guide configured to vary a distance between the second end portion of the elastic compensation member and the first link in a direction perpendicular to a length direction of the first link,
wherein while the movement frame is being moved, the first link is rotated with respect to the first rotational axis, and the compensation member supporting portion rotates with respect to the second rotational axis, and the second end portion of the elastic compensation member is moved with respect to the first link in the length direction of the first link and in the direction perpendicular to the length direction of the first link.

* * * * *